(12) United States Patent
Stellbrink et al.

(10) Patent No.: US 7,654,991 B2
(45) Date of Patent: *Feb. 2, 2010

(54) PRODUCT ARRAY HAVING INDICATORS

(75) Inventors: Beate Rosemarie Stellbrink, Schwalbach (DE); Federica Denti, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 548 days.

This patent is subject to a terminal disclaimer.

(21) Appl. No.: 11/196,840

(22) Filed: Aug. 3, 2005

(65) Prior Publication Data

US 2006/0167425 A1 Jul. 27, 2006

Related U.S. Application Data

(63) Continuation of application No. 11/040,154, filed on Jan. 21, 2005, now Pat. No. 7,175,616.

(51) Int. Cl.
*A61F 13/20* (2006.01)
*A61M 13/32* (2006.01)
*A61F 13/15* (2006.01)
*B65D 83/04* (2006.01)

(52) U.S. Cl. .................. 604/385.17; 604/11; 604/904; 604/385.01; 604/385.06; D24/124; D24/126; 206/529

(58) Field of Classification Search ............... 604/904, 604/11–18, 385.17, 385.01, 385.02; 600/29; D24/141; 206/529
See application file for complete search history.

(56) References Cited

U.S. PATENT DOCUMENTS

| 2,123,750 A | 7/1938 | Schulz |
| 3,738,364 A | 6/1973 | Brien et al. |
| 3,854,481 A | 12/1974 | Messing |
| 3,946,737 A | 3/1976 | Kobler |
| 4,175,561 A | 11/1979 | Hirschman |
| 4,326,527 A | 4/1982 | Wollangk et al. |
| 4,591,523 A | 5/1986 | Thompson |
| 4,609,518 A | 9/1986 | Curro et al. |
| 4,629,643 A | 12/1986 | Curro et al. |

(Continued)

FOREIGN PATENT DOCUMENTS

EP  0 422 660 B1  2/1994

(Continued)

OTHER PUBLICATIONS

PCT International Search Report dated Jul. 28, 2006.

*Primary Examiner*—Jacqueline F. Stephens
(74) *Attorney, Agent, or Firm*—James E. Oehlenschlager; Jason J. Camp; Roddy M. Bullock

(57) ABSTRACT

An array of disposable absorbent articles having a first article and a second article. The first article has an outer surface wherein the outer surface has an outer surface area and a first identifier having a first surface area. The first identifier is disposed on the first article and corresponds to a first performance characteristic. The second article has an outer surface wherein the outer surface has an outer surface area and a second identifier having a second surface area. The second identifier is disposed on the second article and corresponds to a second performance characteristic. The first article is a different article than said second article.

17 Claims, 8 Drawing Sheets

U.S. PATENT DOCUMENTS

| | | |
|---|---|---|
| 4,685,178 A | 8/1987 | Nakanishi |
| 4,839,216 A | 6/1989 | Curro et al. |
| 4,951,368 A | 8/1990 | Heinen |
| 5,153,971 A | 10/1992 | Van Iten |
| 5,350,371 A | 9/1994 | Van Iten |
| 5,592,725 A | 1/1997 | Brinker |
| 5,738,646 A | 4/1998 | Fox et al. |
| 5,788,910 A | 8/1998 | McNelis et al. |
| 5,832,576 A | 11/1998 | Leutwyler et al. |
| 5,891,081 A | 4/1999 | McNelis et al. |
| 5,911,712 A | 6/1999 | Leutwyler et al. |
| 5,958,321 A | 9/1999 | Schoelling et al. |
| 6,003,216 A | 12/1999 | Hull, Jr. et al. |
| 6,071,259 A | 6/2000 | Steiger et al. |
| 6,093,027 A | 7/2000 | Unger et al. |
| 6,156,021 A | 12/2000 | Tojkander |
| 6,283,952 B1 | 9/2001 | Child et al. |
| 6,310,269 B1 | 10/2001 | Friese et al. |
| 6,601,705 B2 | 8/2003 | Molina et al. |
| 2002/0016579 A1 | 2/2002 | Stenberg |
| 2002/0151859 A1 | 10/2002 | Schoelling |
| 2002/0183681 A1 | 12/2002 | Bernard |
| 2003/0078553 A1 | 4/2003 | Wada et al. |
| 2003/0106825 A1 | 6/2003 | Molina et al. |
| 2003/0236485 A1 | 12/2003 | Fedyk et al. |
| 2004/0050738 A1 | 3/2004 | Molina et al. |
| 2004/0102748 A1 | 5/2004 | Hirotsu |
| 2004/0122284 A1 | 6/2004 | Zunker |
| 2006/0069372 A1 | 3/2006 | Chakravarty et al. |
| 2006/0129114 A1 | 6/2006 | Mason, Jr. et al. |
| 2006/0129116 A1 | 6/2006 | Hughes et al. |
| 2006/0135927 A1 | 6/2006 | Zander et al. |

FOREIGN PATENT DOCUMENTS

| | | |
|---|---|---|
| EP | 1 481 656 | 12/2004 |
| EP | 1 666 012 | 6/2006 |
| WO | WO 00/37013 A1 | 6/2000 |
| WO | WO 01/66055 A1 | 9/2001 |
| WO | WO 02/30347 | 4/2002 |
| WO | WO 02/078586 A3 | 10/2002 |

PRODUCT ARRAY HAVING INDICATORS

CROSS REFERENCE TO RELATED APPLICATION

This application is a continuation of U.S. application Ser. No. 11/040,154 filed Jan. 21, 2005, now U.S. Pat No. 7,175,616.

FIELD OF THE INVENTION

This invention relates to a product array which signal a common indicator, and more particularly to disposable absorbent articles comprising a common indicator within a product array.

BACKGROUND OF THE INVENTION

Often manufacturers and marketers of consumer products wish to appeal to consumers of related goods, products, or services. For example, a consumer of digital tampons may also purchase sanitary napkins. Likewise, a consumer of tampon applicators may wish to purchase pantiliners. In general, many products have related benefits and performance characteristics such as absorbency but are marketed under different brands, or by different companies, so that consumers cannot make a connection between the different products resulting in a purchasing decision. Thus, a manufacturer and marketer of two brands of products may wish to co-market the two brands so that consumers can easily identify both brands.

Co-marketing, or co-merchandising, that is, advertising or displaying products together in a retail environment so as to prompt a purchasing decision of one or both of the products based on the association of the two in the retail environment is known. Accordingly, it would be desirable to have a product array of marketing products in which a consumer can associate a performance characteristic from one product with another product without reference to printed text, pictures, diagrams, labels, and combinations thereof located on the package. Further, it would be desirable to have a retail display in which two or more branded products with a common performance characteristic would have a common indicator to help the consumer during shopping. Additionally, it would be desirable to have an improved method for prompting purchasing decisions in which a consumer of one brand is encouraged to purchase a different brand.

SUMMARY OF THE INVENTION

An array of disposable absorbent articles having a first article and a second article. The first article has an outer surface wherein the outer surface has an outer surface area and a first identifier having a first surface area. The first identifier is disposed on the first article and corresponds to a first performance characteristic. The second article has an outer surface wherein the outer surface has an outer surface area and a second identifier having a second surface area. The second identifier is disposed on the second article and corresponds to a second performance characteristic. The first article is a different article than the second article.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
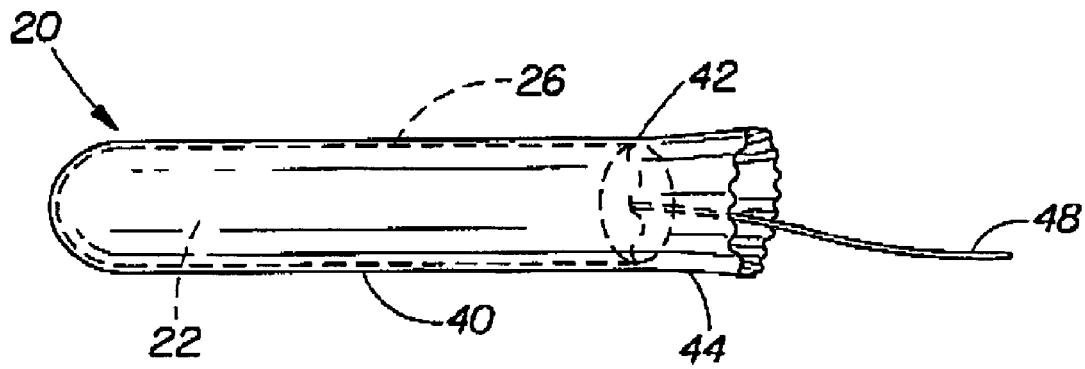
FIG. 1 is a perspective view of a tampon of the present invention incorporating a compressed absorbent member and an overwrap covering the exterior surface and forming a skirt.

Section A will provide terms which will assist the reader in best understanding the features of the invention but not to introduce limitations in the terms inconsistent with the context in which they are used in this specification. These definitions are not intended to be limiting. Section B will discuss the tampon of the present invention. Section C will discuss the tampon applicator of the present invention. Section D will discuss the sanitary napkin of the present invention. Section E will discuss the incorporation of the indicators into products which are the novel features of the present invention.

A. Terms

"Absorbent articles" as referred to herein are primarily sanitary napkins, sanitary panties, interlabial devices, intravaginal devices (tampons), adult incontinence products, infant diapers, pantiliners, and the like. Theses articles have been described in the extensive patent literature and many such articles are in the stream of commerce. See, for example, for sanitary napkins, U.S. Pat. No. 4,463,045 issued to Ahr et al. and U.S. Pat. No. 4,556,146 issued to Swanson et al.; for tampons, U.S. Pat. No. 5,087,239 issued to Beastall et al. and U.S. Pat. No. 5,279,541 issued to Frayman et al.; and for diapers, U.S. Pat. No. 4,573,986 issued to Minetola et al.; U.S. Pat. No. 4,695,278 issued to Lawson; U.S. Pat. No. 4,081,301 issued to Buell; and U.S. Pat. No. 4,515,595 issued to Kievit. Typically, the disclosed absorbent articles contain an absorbent structure in the form of a "core" or a pad. Various fluid-permeable topsheets, fluid-impermeable backsheets, panty-protective "wings," tape fasteners are optionally used to construct elements for such articles and are all within the experience of those of ordinary skill in the art.

The term, "surface area" as used herein refers to the measure of any two-dimensional figure within a 1 cm by 1 cm measured portion, such that two surface areas may be compared relatively to one another. While the measured portion will have a defined dimension, the surface area within that portion will always be different from the defined dimension if the product has topographical features such as protuberances, depressions, and grooves present within the measured portion. Any known method may be used so long as the measurement does not alter or otherwise distort the surface area, such as by swelling the materials. The preferred method of measure involves image analysis using any image analysis software or algorithm for assessing surface area. It should be understood that the surface area of interest is that which is apparent at the millimeter scale using light microscopy or macrophotography. As well, it should be noted that the surface area is not at the molecular or atomic scale, e.g. techniques such as AFM or BET are not useful herein.

As used herein, "indicator" refers to a signal perceptible to the user that corresponds to a functionally distinguishable characteristic of a feminine hygiene article. In a system of products, the functionally-distinguishable characteristic of a feminine hygiene article is a characteristic that is different in surface area from other products in the same array. The indicator can be any indicia and/or shape. As used herein, indicia is any identifying marking, which may include words and/or graphics identifying the product in use.

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

As used herein, the term "density" is used with its common technical meaning with units of $g/cm^3$ or g/cc. The density may refer specifically to that of a specific region or feature of the tampon as noted. The density will be measured, unless otherwise noted, by taking the weight divided by the geometric volume described by the shape. Unless noted, density refers to that of the overall structure and not the individual components, and will include in the measurement void volume of small pores and voids within the overall structure.

The term "digital tampon" refers to a tampon which is intended to be inserted into the vaginal canal with the user's finger and without the aid of an applicator. Thus, digital tampons are typically visible to the consumer prior to use rather than being housed in an applicator.

The term "folded" as used herein, is the configuration of the tampon pledget that may be incidental to lateral compaction of the absorbent material or may purposely occur prior to a compression step. Such a configuration is readily recognizable, for example, when the absorbent material abruptly changes direction such that one part of the absorbent material bends and lies over another part of the absorbent material.

As used herein, "generally cylindrical" refers to the usual shape of tampons as is well known in the art, but which also includes oblate or partially flattened cylinders, curved cylinders, and shapes which have varying cross-sectional areas (such as a Coke™ bottle shape). The longitudinal axis refers to the longest linear dimension of the tampon. The cross-section refers to a slice taken at right angles to the longitudinal axis.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 2:
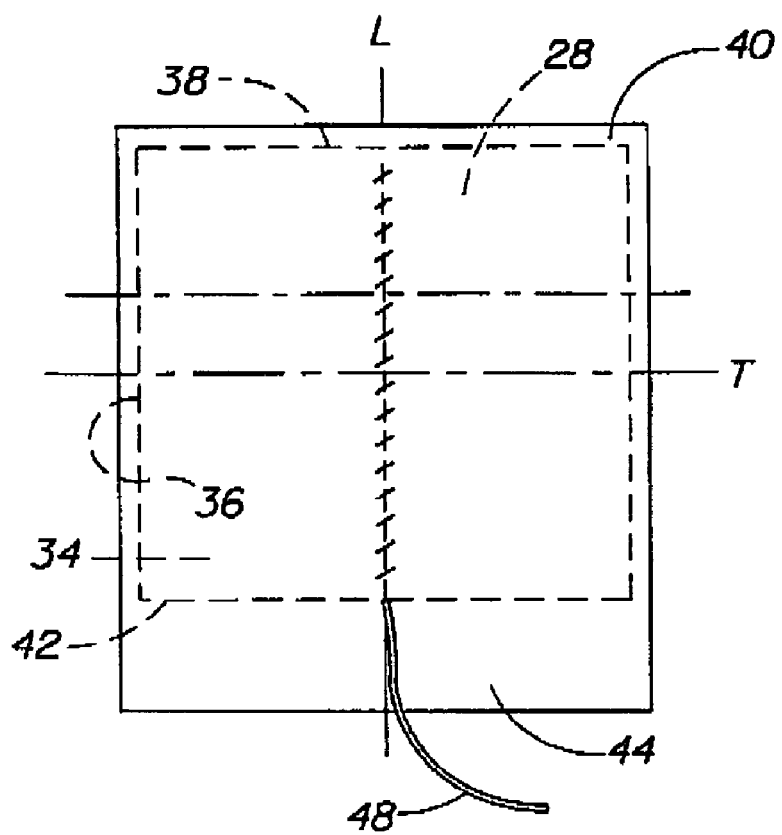
FIG. 2 is a plan view of an assembled absorbent material and overwrap prior to compression.

As used herein, the term "longitudinal axis" of a tampon refers to the axis that runs through the center of the tampon as shown in FIG. 2. A portion of the tampon may be asymmetric about the longitudinal axis, such as when the withdrawal end region is flared and distorted from the original shape of the rest of the tampon (such as a "fin shape"). Further, the longitudinal axis may be linear or non-linear.

The "outer surface" of a product refers to the visible surface of the (compressed and/or shaped) product prior to use and/or expansion. At least part of the outer surface may be smooth or alternatively may have topographic features, such as ribs, spiraling ribs, a mesh pattern, or other topographical features. If the product is a tampon, typically, tampons are constructed from an absorbent material, which has been compressed and/or shaped in any or all of the width direction, the radial direction, and the axial direction, in order to provide a tampon which is of a size and stability to allow insertion within the vagina or other body cavity.

The term "cross-section," as used herein, is any 5 mm thick section orthogonal to the longitudinal axis.

As used herein, the terms "pledget" or "tampon pledget" are intended to be interchangeable and refer to a construction of absorbent material prior to the compression and/or shaping of such construction into a tampon as described above. Pledgets may be rolled, folded or otherwise manipulated prior to compression. Tampon pledgets are sometimes referred to as tampon blanks, or a softwinds, and the term "pledget" is intended to include such terms as well. In general in this specification, the term "tampon" is used to refer to a finished tampon after the compression and/or shaping process. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein, a tampon has a "self-sustaining shape" when a tampon pledget has been compressed and/or shaped such that it assumes a general shape and size, which is vaginally insertable, absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein, the term "tampon" refers to any type of absorbent structure that can be inserted into the vaginal cavity or other body cavities for the absorption of fluid therefrom or for the delivery of active materials, such as medicaments or moisture. A tampon can be straight or non-linear in shape, such as curved along the longitudinal axis.

Generally, there are two types of tampons. The first type of tampon is a self-sustaining tampon. Tampons are generally "self-sustaining" in that they will tend to retain their general shape and size before use. A typical self-sustaining tampon is 35-60 mm long, the length measured from the top of the tampon to the base of the tampon along a longitudinal axis. The measurement to the base of the tampon does not include any overwrap, secondary absorbent member, or withdrawal cord which extends beyond the tampon's main absorbent material. A typical self-sustaining tampon is 5-20 mm wide corresponding to the largest cylindrical cross section. The width can vary along the length of the self-sustaining tampon.

The second type of tampon is an easily "deformable, fluid-permeable bag tampon". The deformable, fluid-permeable bag tampon consists of, but is not limited to, pieces such as absorbent chips, spheres, or fibers such that the fluid permeable bag tampon is readily deformable with a force of less than about 3 psi. The tampon is substantially deformable at pressures of less than about 1 psi; resulting in the tampon spreading or being easily indented when the pressure is applied from a surface of about 0.15 mm diameter.

As used herein, "tampon applicator" refers to a device or implement that facilitates the insertion of a tampon, medicament, treatment device, visualization aid, or other into an external orifice of a mammal, such as the vagina, rectum, ear canal, nasal canal, or throat. Non-limiting specific examples of such include any known hygienically designed applicator that is capable of receiving a tampon may be used for insertion of a tampon, including the so-called telescoping, tube and plunger, and the compact applicators, an applicator for providing medicament to an area for prophylaxis or treatment of disease, a spectroscope containing a microcamera in the tip connected via fiber optics, a speculum of any design, a tongue depressor, a tube for examining the ear canal, a narrow hollow pipe for guiding surgical instruments, and the like.

As used herein, the terms "vaginal cavity" and "within the vagina" refer to the internal genitalia of the human female in the pudendal region of the body.

B. General Descpription of Basis Parts of a Tampon

FIG. 1 shows a general tampon 20. The tampon 20 can be any shape in the art and any type of tampon known in the art. In one non-limiting example, tampon 20 could be a shaped tampon 20, such as that disclosed in U.S. Pat. No. 6,824,536. FIG. 1 illustrates a tampon 20 for feminine hygiene.

Referring to FIGS. 1-2, in general, tampon 20 comprises a compressed absorbent member 22 which comprises absorbent material 28 and a fluid permeable overwrap 40 that covers absorbent member 22. Overwrap 40 may extend beyond one end of absorbent member 22 to form a skirt portion 44. A removal means, such as string 48 can be provided to facilitate removal of the tampon 20 after use. Tampons, including overwraps for use as the body contacting surface thereof, are well known in the art and need no detailed description of various alternative and optional designs.

Each major element of the tampon 20 is described below.

i. Absorbent Material

Referring to FIG. 2, the absorbent material 28 may be any suitable size and thickness suitable for compression into a tampon 20 (FIG. 1) having a vaginally insertable shape. In the embodiment shown in FIG. 2, the absorbent material 28 is generally square or rectangular, but other shapes such as trapezoidal, triangular, hemispherical, chevron and hourglass shaped are also acceptable. A more detailed description of liquid-absorbing materials and pledget shapes and dimensions can be found in currently pending and commonly assigned, U.S. patent Ser. No. 10/039,979, filed Oct. 24, 2001, entitled "Improved Protection and Comfort Tampon," to Agyapong, et al.

The absorbent material 28 may comprise a folded structure or may be rolled. The resulting compressed absorbent member 22 (FIG. 1) of the tampon 20 may be constructed from a wide variety of liquid-absorbing materials commonly used in absorbent articles such as rayon (including tri-lobal and conventional rayon fibers), cotton, or comminuted wood pulp which is generally referred to as airfelt. Examples of other suitable absorbent materials 28 include creped cellulose wadding; meltblown polymers including coform; chemically stiffened, modified or cross-linked cellulosic fibers; synthetic fibers such as crimped polyester fibers; foam; tissue including tissue wraps and tissue laminates; or any equivalent material or combinations of materials, or mixtures of these.

Pressures and temperatures suitable for compression are well known in the art. Typically, the absorbent material 28 and the overwrap 40 are compressed in the radial direction and optionally axially by any means well known in the art. While a variety of techniques are known and acceptable for these purposes, a modified tampon compressor machine available from Hauni Machines, Richmond, Va., is suitable.

The fibrous material of the tampon 20 of the present invention may have uniform density over a cross section of the tampon 20. Alternatively, fibrous material of the tampon 20 may have varying density over a cross section of the tampon 20. A tampon 20 having varying densities is described in greater detail in co-pending patent application filed Nov. 4, 2003, entitled "Substantially Serpentine Shaped Tampon with Varying Density Regions", to Almond, Docket Number 9419 and co-pending patent application filed Nov. 4, 2003, entitled "Substantially Serpentine Shaped Tampon with Varying Density Regions", to Almond, Docket Number 9418.

ii. Overwrap Referring to FIG. 2, in the embodiments shown, the overwrap material 40 is generally rectangular, but other shapes such as trapezoidal, triangular, hemispherical, chevron, hourglass shaped, "T" and "L" shaped are also acceptable. Optimally, the overwrap 40 may correspond to the shape of the absorbent material 28. The overwrap 40 is positioned around the absorbent material 28 so that the overwrap 40 may be proximate with the insertion end 38 of the absorbent material 28. In this regard, the overwrap 40 could exactly match up to the insertion end 38 or could for example extend from about 2 mm to about 8 mm over the insertion end 38. As well, the overwrap 40 may extend beyond the withdrawal end 42 to form a skirt portion 44 as discussed below.

Because the overwrap 40 can be wrapped in the various configurations, the width of the overwrap 40 may vary. The width of the overwrap 40 may be wider or less wide than the measure of the longitudinal or transverse axis of the absorbent material 28 it is being wrapped around.

The overwrap 40 substantially covers both the first surface 34 and the second surface 36 of the absorbent material 28. "Substantially covers" in this case means that the overwrap 40 covers at least about 75%, optionally at least about 90% of the combined surface area of the first surface 34 and the second surface 36. The overwrap 40 may be wrapped around the longitudinal axis "L" or the transverse axis "T" as shown in the attached figures in another embodiment. As well, two or more separate pieces of overwrap 40 can sandwich the absorbent material 28.

The overwrap 40 may be joined to the absorbent material 28 by any variety of means. The overwrap 40 may be joined to itself or to the absorbent material 28. For example, one portion of overwrap 40 may be joined to an opposed portion of the overwrap 40 or the absorbent material 28 using any suitable adhesive or heat/pressure bonding means. Such adhesive may extend continuously along the length of attachment or it may be applied in a "dotted" fashion at discrete intervals. One method of heat bonding includes thermally bonding, fusion bonding, or any other suitable means known in the art for joining such materials. Alternatively, the overwrap 40 may be joined to the absorbent material 28 along with the withdrawal cord 48 by sewing as shown in FIG. 2. Such sewing may use natural or synthetic thread.

A more detailed description of the material of the overwrap 40 can be found in currently pending and commonly assigned, U.S. patent Ser. No. 10/719,793, filed Nov. 21, 2003, entitled "Tampon with Raised Portions," to Edward Paul Carlin.

iii. Skirt Portion/Secondary Absorbent

Referring to FIG. 2, the overwrap 40 may extend beyond the withdrawal end 42 to form a skirt portion 44. The length of the skirt portion 44 is not critical. Typically, the overwrap 40 can extend from about 2 mm to about 30 mm beyond the withdrawal end 42 of the absorbent material 28. Typically, the overwrap 40 extends from about 5 mm to about 20 mm beyond the withdrawal end 42 of the absorbent material 28. In one embodiment, the skirt portion 44 may not be compressed.

Referring to FIG. 1, both the compressed absorbent member 22 and skirt portion 44 of the overwrap 40 may reside entirely within the vaginal cavity of the wearer during use of the tampon 20. This is achieved by the relative closeness of the skirt portion 44 to the withdrawal end 42 of the absorbent material 28 as well as of the relative size compared to the overall size of the tampon 20. In particular embodiments, only the withdrawal cord 48 or other withdrawal means resides externally to the orifice of the vagina.

The tampon of the present invention may comprise a secondary absorbent member such as that disclosed in U.S. Pat. Nos. 6,258,075 and 6,599,279.

C. General Descpription of Basis Parts of a Tampon Applicator

Figure 3:
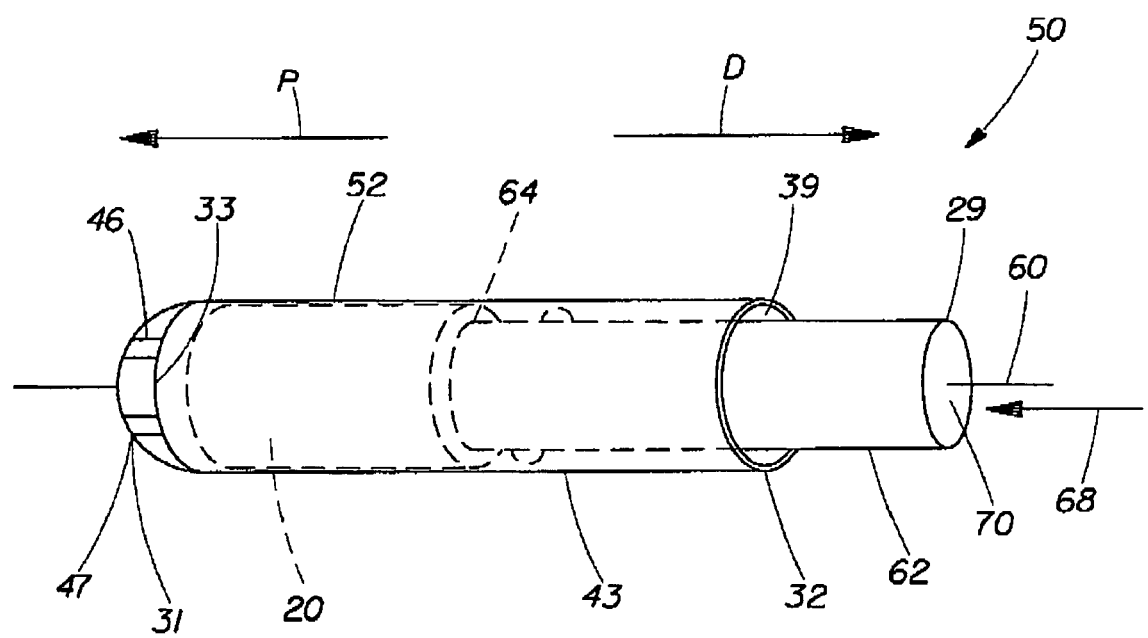
FIG. 3 is a perspective view along a longitudinal axis of a tampon applicator of the present invention.

Referring to FIG. 3, a tampon applicator 50 is shown which is designed to position tampon 20 inside the vaginal cavity. Also, FIG. 3 shows "proximal" and "distal" designated as P and D, respectively. The tampon applicator 50 may be used with any type of tampon 20. The tampon 20 could be a self-sustaining tampon or a deformable fluid permeable bag tampon.

Generally, the tampon applicator 50 includes an outer member 52 and an inner member 62. The outer member 52 comprises an insertion end 31 and a second end 32 opposed to the insertion end 31. During insertion of the tampon applicator 50 into the body of a wearer, the insertion end 31 is the most proximal end to the body of the wearer along the longitudinal axis 60 and the second end 32 is the most distal end to the body of the wearer along the longitudinal axis 60. A preformed hinge or groove 33 may extend around the periphery of the outer member 52 near the insertion end 31. The outer member 52 may also have a dome-shaped end having a number of radial slits 46 therein extending from a central aperture to the groove 33. The portion of the outer member 52 adjacent to the insertion end 31 may also have an openable end, such as petals 47. In addition, the outer member 52 can contain a grip region 43 located adjacent to the second end 32 of the outer member 52.

The inner member 62 is dimensioned to slidably move within the hollow interior portion 39 of the outer member 52, with minimal clearance therebetween. The inner member 62 has a first end 64 and a second end 29 opposed to the first end 64. The first end 64 is the most proximal end of the inner member 62 along the longitudinal axis 60. In this embodiment, the first end 64 provides the necessary force to expel the tampon 20. The second end 29 is the most distal end of the inner member 62 along the longitudinal axis 60. An axial force 68 is applied to the second end 29 of inner member 62 to expel the tampon 20. Also, the inner member 62 can have a hollow interior portion 70. Alternatively, the inner member 62 can be solid or partially solid.

The tampon applicator 50 has a pre-expelled state and a partially expelled state. During the pre-expelled state, as is readily seen in FIG. 3, the tampon 20 sits within the outer member 52 and is substantially aligned with the tampon applicator 50. The tampon 20 can remain snugly therein without any outside force to sustain its position in the tampon applicator 50.

Figure 4:
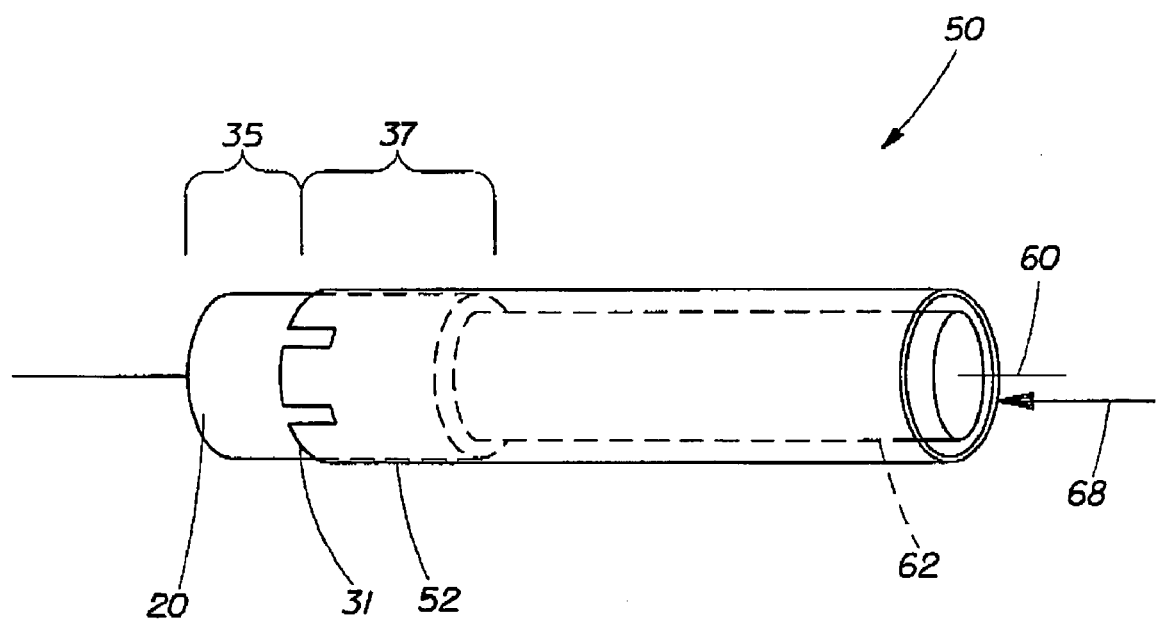
FIG. 4 is a perspective view of the tampon applicator of the present invention when the tampon applicator is fully engaged.

As is readily seen in FIG. 4, when the axial force 68 is applied along the longitudinal axis 60, the inner member 62 slides toward the insertion end 31 of the outer member 52. The inner member 62 bears against the rear end of tampon 20 pushing the tampon 20 toward the insertion end 31 of outer member 52. Upon full engagement of inner member 62 with outer member 52, the exposed portion 35 of the tampon 20 is expelled from the tampon applicator 50 and a remaining portion 37 of the tampon 20 can be contained within the tampon applicator 50.

D. General Descpription of Basis Parts of a Sanitary Napkin

The below disclosure is meant to give a general description of the basic parts of sanitary napkins, incontinence pads, and the like as they are known in the art. The description is not intended to be limiting. Any and all of various known elements, features and processes of known sanitary napkins, pantiliners, incontinence pads, and the like can be incorporated in the feminine hygiene article of the present invention as desired or needed for particular use benefits. For example, sanitary napkins can be according to the disclosure of U.S. Pat. No. 4,950,264 issued to Osborn III Aug. 21, 1990, and an incontinence pad can be according to the disclosure of U.S. Pat. No. 5,439,458 issued to Noel et al. Aug. 8, 1995. Now, with respect to the remaining disclosure, the novel features and benefits of the present invention will be described.

Figure 5:
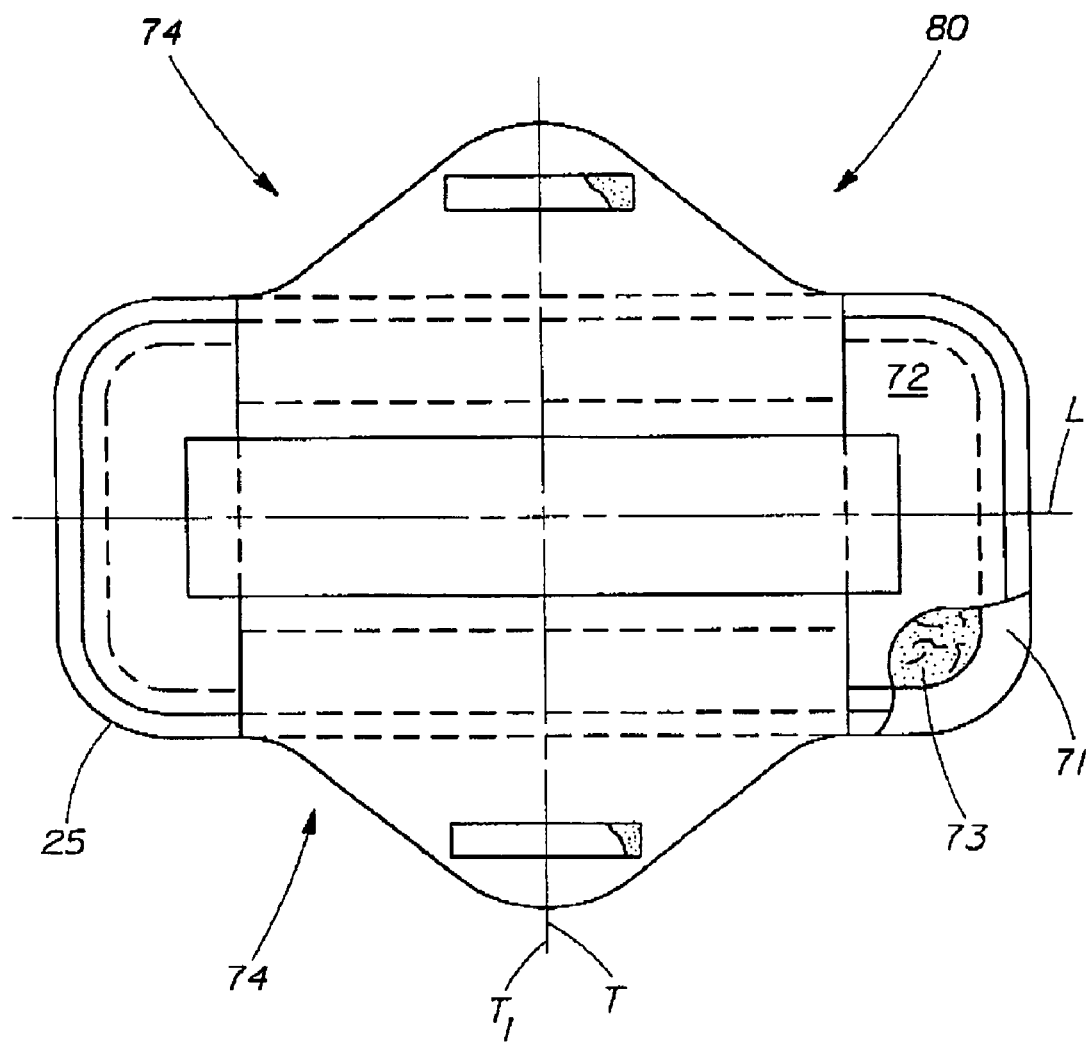
FIG. 5 is a top plan view of a sanitary napkin embodiment of the present invention with portions cut away to reveal the underlying structure of the sanitary napkin.

FIG. 5 shows a plan view of a sanitary napkin 80 of the present invention. The absorbent article according to the present invention is conventionally constructed of three main elements: the topsheet 71, the backsheet 72, and the absorbent element 73 disposed between the topsheet 71 and backsheet 72. The topsheet 71 faces the user of the article during use and is liquid pervious in order to allow liquids to pass into the sanitary napkin 80. The topsheet 71 can be an apertured topsheet 71. The backsheet 72 provides liquid containment such that absorbed liquid does not leak through the article. The backsheet can be joined about the periphery 25. Optionally, sanitary napkin 80 can have side extensions, commonly referred to as "wings" 74 designed to wrap the sides of the crotch region of the panties of the user of sanitary napkin 80. Sanitary napkins 80, including topsheets 71 for use as the body facing surface thereof, are well known in the art and need no detailed description of various alternative and optional designs.

E. Incorporation of Indicators into Products

The above disclosure is meant to give a general description of the basic parts of feminine hygiene articles such as tampons, tampon applicators, sanitary napkins and the like as they are known in the art. The description is not intended to be limiting. Any and all of various known elements, features and processes of known tampons, tampon applicators, sanitary napkins, and the like can be incorporated in the feminine hygiene article of the present invention as desired or needed for particular use benefits. Now, with respect to the remaining disclosure, the novel features and benefits of the present invention will be described.

In its broadest aspect, the present invention is directed to an array of disposable absorbent articles comprising a line-up of disposable absorbent articles in which each disposable absorbent article of the product array comprises the same or substantially the same indicator. When so employed, the surface area that the indicator covers provides an easy and intuitive method for indicating the absorbency of the product which is either on the product and/or on the package. When indicators are placed on the product, the indicator provides a method for selecting the proper absorbency for the products independent the package. Thus, when the article is then removed from the original container and placed in the bathroom drawer, purse, etc. the user can select the proper absorbency product. Additionally, when the indicator is placed on the package it helps the consumer select the right product.

Moreover, by the present invention, a system of distinct indicators is used to implement the proper selection and use of consumer products, including catamenials, especially tampons, sanitary napkins, and interlabial devices. The present invention may also be used in other fields such as beauty care, food and beverage, health care, laundry and cleaning, and tissues and towels. For example, indicators may be used in beauty care to denote product performance characteristics such as more or less moisture; in coffee products to differentiate between light, medium, and dark roast levels; in the health care area to denote stronger medicine such as cough drops and chloraseptics; in laundry and cleaning to indicate a higher concentration of detergent; and in tissues and towels to denote levels of absorbency. The use of common indictors across a product array in this manner univocally and unequivocally connotes performance characteristics, thereby improving user satisfaction with the product and decreased anxiety in choosing the correct product.

The indicators are perceived and referred to in terms of the amount of surface area that is covered by the absorbent article. Typically, the more surface area that the indicator covers the greater the absorbency that the indicator indicates.

Figure 6:
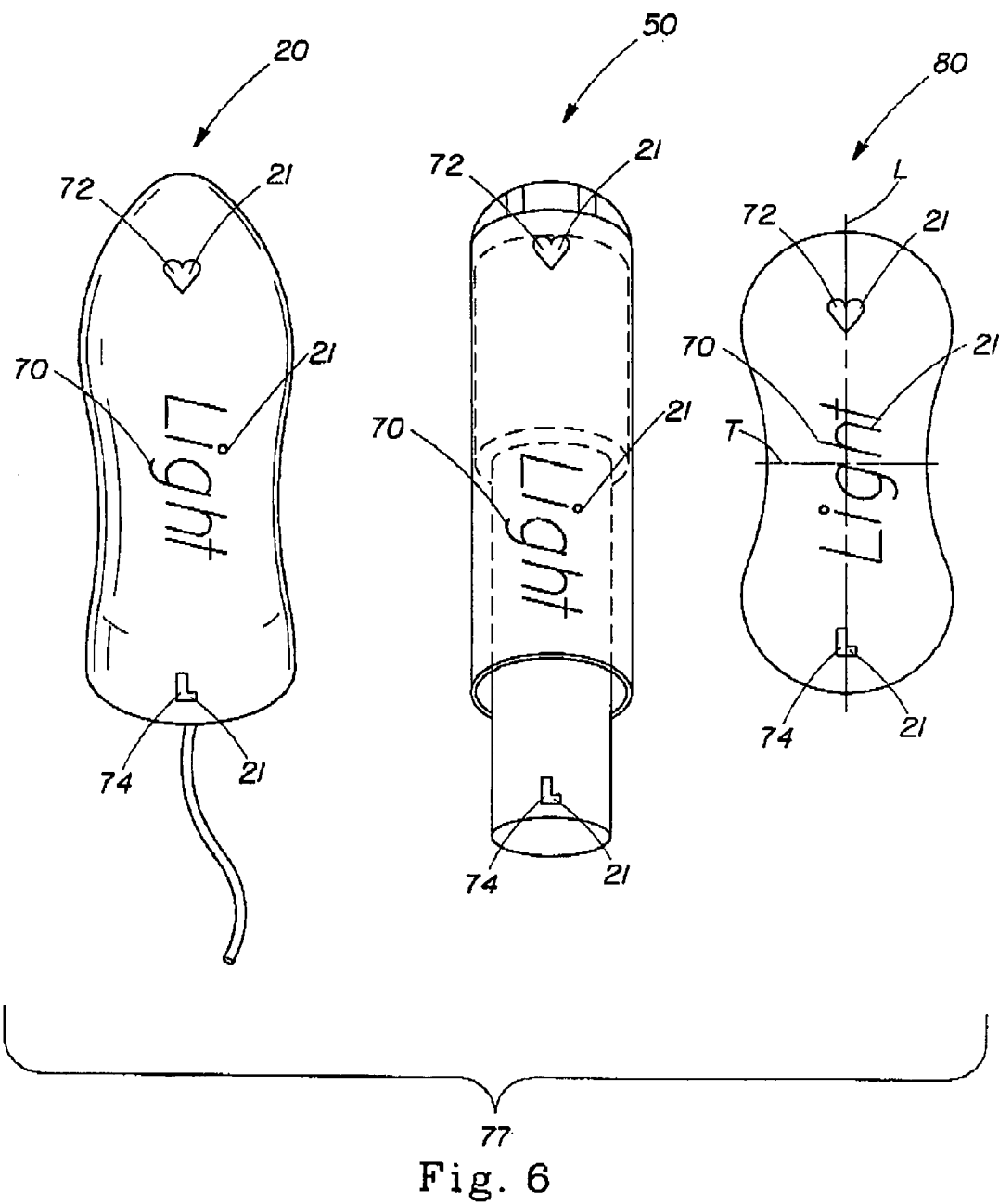
FIG. 6 is a view of an array of feminine hygiene articles of the present invention.
Figure 7:
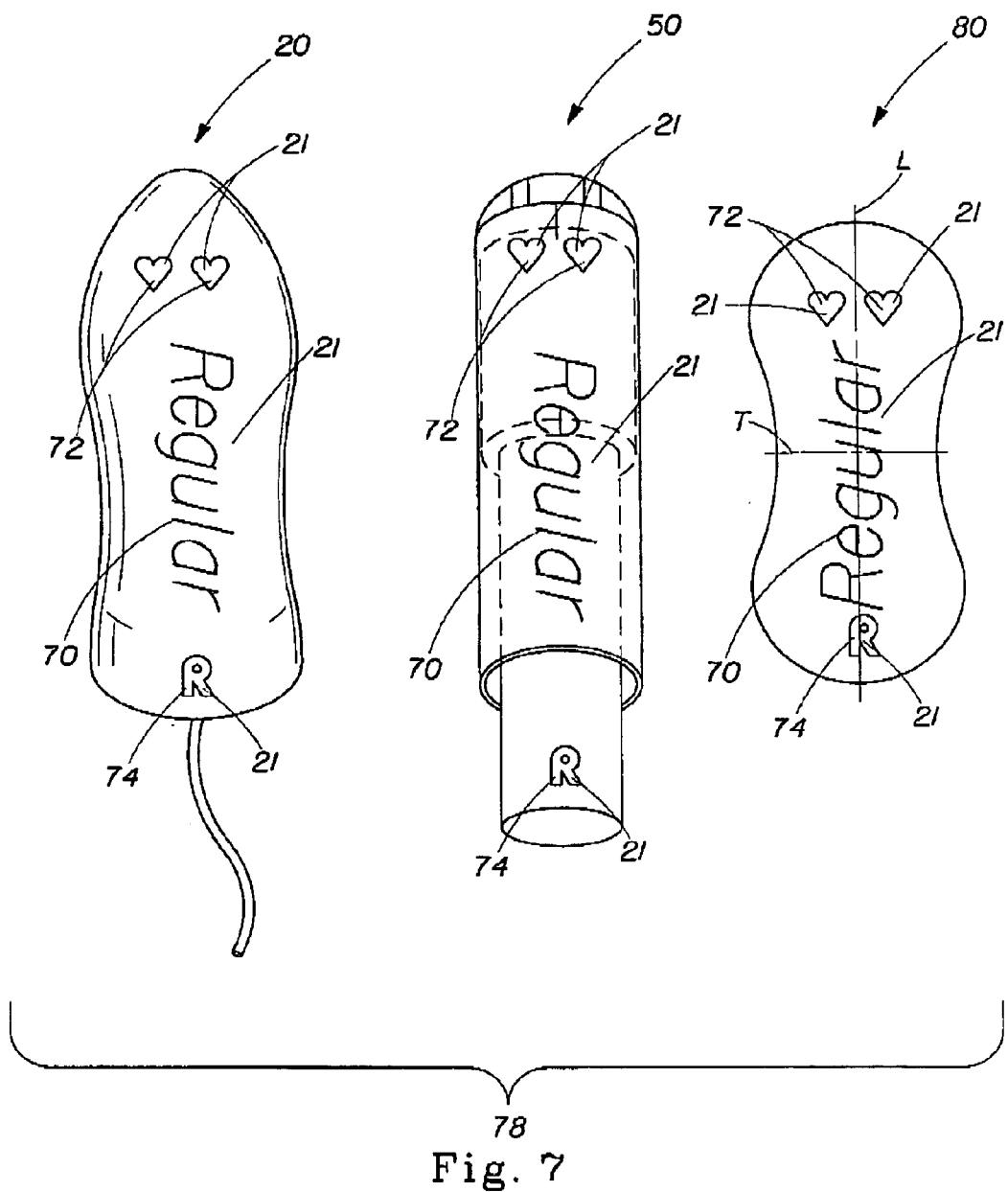
FIG. 7 is a view of an array of feminine hygiene articles of the present invention.
Figure 8:
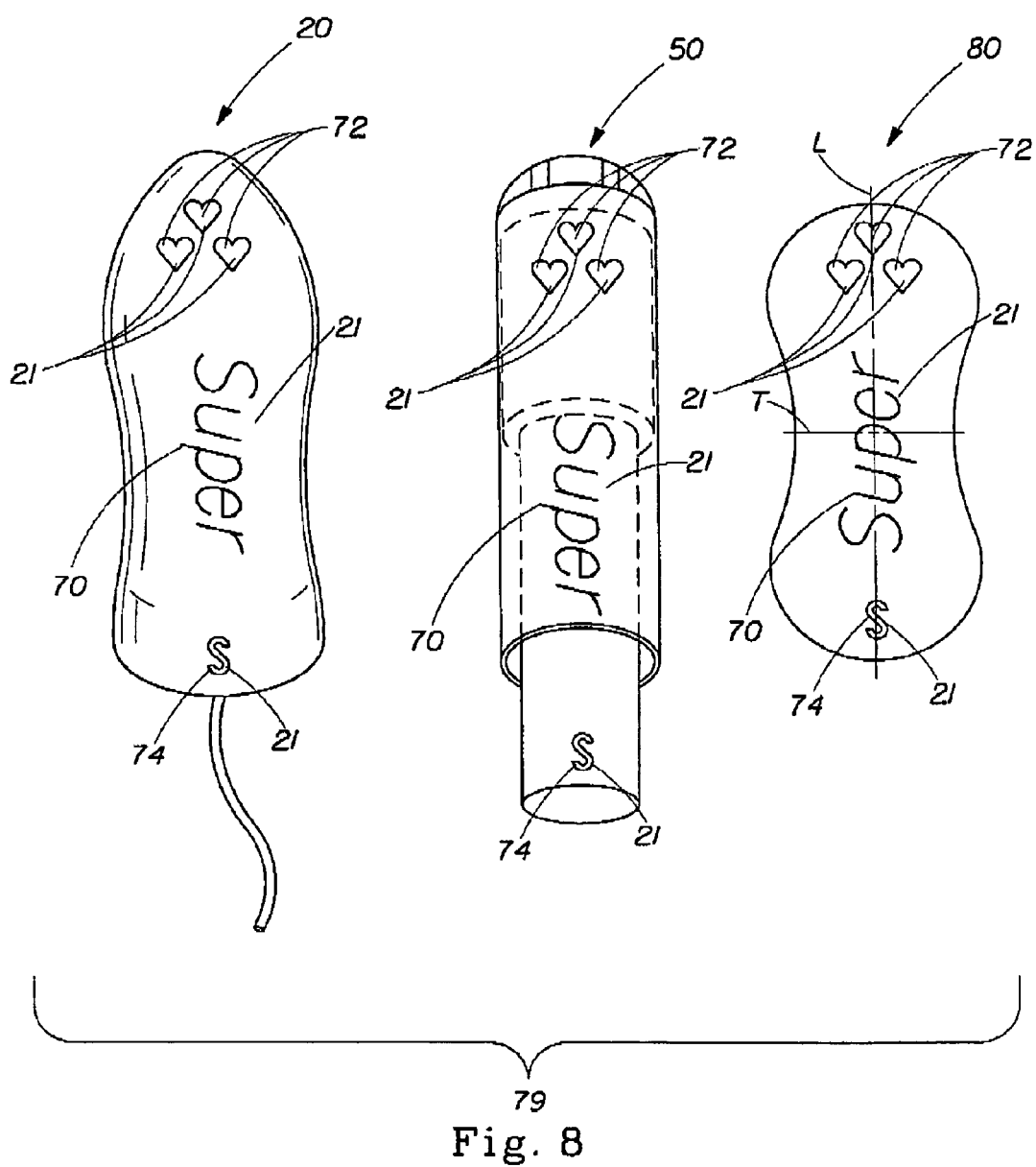
FIG. 8 is a view of an array of feminine hygiene articles of the present invention.

In one non-limiting example, as shown in FIGS. 6-8, three product arrays for light absorbency 77 (FIG. 6), regular absorbency 78 (FIG. 7), and super absorbency 79 (FIG. 8) are shown. Each product array 77 (FIG. 6), 78 (FIG. 7), 79 (FIG. 8) each consist of tampons 20, tampon applicators 50, and sanitary napkins 80 having a plurality of indicators 21. As shown, each product 20, 50, 80 in each array 77 (FIG. 6), 78 (FIG. 7), 79 (FIG. 8) can have information-bearing written indicia 70 to literally "spell out" the functional characteristic of each array 77 (FIG. 6), 78 (FIG. 7), 79 (FIG. 8), such as light absorbency, regular absorbency, or super absorbency capacity. In addition, or separately, the arrays 77 (FIG. 6), 78 (FIG. 7), 79 (FIG. 8) can be differentiated by the number of visually distinct pattern elements 72 such as the heart shapes shown in FIG. 6. Thus, the greater number of hearts, the greater the characteristic signaled by the indicator 21. In addition, or separately, the indicator 21 can include a shortened form of the information-bearing written indicia 74, such as "L" for light absorbency, "R" for regular absorbency, and the "S" for super absorbency.

In another non-limiting example of direct information-bearing signals to the user, feminine hygiene articles, such as tampons, pantiliners, and an adult incontinences, can have indicators that provide direct information-bearing signals to the user, such as numerals or written indicia that communicate information by way of clearly understood gradations in scale. For example, each array of tampons, pantiliners, and an adult incontinences can be identified by a number, with increasing numbers indicating an increase in a functional characteristic. For example, increasing numbers can signal an increasing amount of absorbent capacity relative to lower-numbered articles. For example, the first array can have the numeral "3" representing high absorbent capacity, the second array can have the number "2" representing medium absorbent capacity, and the third array can have the number "1" representing low absorbent capacity. The increasing numerals can signal more absorbent capacity across each array.

In another non-limiting example, in the context of one embodiment of the present invention, an array consists of a digital tampon, a pantiliner, and a sanitary napkin. The arrays are "mini" absorbency, "normal" absorbency, "super" absorbency, and "super plus" absorbency. The products in the array which signal a "mini" absorbency have indicators which are six grooves. Thus, the tampon has six grooves, the panitliner has six grooves, and the sanitary napkin has six grooves. The products in another array which signal "normal" absorbency have indicators which are twelve grooves. Thus, the tampon has twelve grooves, the panitliner has twelve grooves, and the sanitary napkin has twelve grooves. The products in the array which signal "super" absorbency have indicators which are fifteen grooves. Thus, the tampon has fifteen grooves, the panitliner has fifteen grooves, and the sanitary napkin has fifteen grooves. The products in the array which signal "super plus" absorbency have indicators which are twenty grooves. Thus, the tampon has twenty grooves, the panitliner has twenty grooves, and the sanitary napkin has twenty grooves. It will be appreciated by those skilled in the visual arts that the number of grooves are relative, not absolute, terms that can be used to compare the surface areas with each other.

With such a line up, the consumer is able to remember easily that less surface area corresponds to lower absorbency while higher absorbency corresponds to a higher surface area. Preferably, the variation in surface area is great enough to be readily perceived by a consumer without having to refer to an external basis or calibration means for comparison. For example, if the product performance characteristic being represented is absorbency, an indicator covering about 24% of the surface area of the product in the product array might represent low absorbency. An indicator covering about 46% of the surface area of the product in the product array might represent high absorbency, while an indicator covering about 41% of the surface area of the product in the product array might represent regular absorbency.

The product herein is displayed in a manner such that the consumer's attention is drawn to the entire product line. The product line may contain two or more products. For example, the two or more products can have the same or substantially the same indicators. Thus, on a store shelf or display rack, the products have the gradation of absorbencies are preferably placed in a side-by-side array, most preferably in ascending order of absorbency. The ascending order may be from left to right; right to left; up to down; down to up; horizontally; or diagonally. It is noted that side-by-side herein means that all articles in the product line are in sufficient proximity to each other, either horizontally, vertically, or diagonally to be within the consumer's zone of perception at the same time. The products should be in close enough proximity to prevent undue confusion for the consumer. Thus, in a horizontal display reading from left-to-right, products having low absorbency (indicators covering less surface area), medium absorbency (indicators covering more surface area than the low absorbency tampon but the indicators covering less surface area coverage than the high absorbency tampon), and high absorbency (indicators covering more surface area than the medium absorbency tampon) are displayed together. This not only draws attention to the entire product line, but also provides additional visual signals to the consumer by virtue of the side-by-side display.

Figure 9:
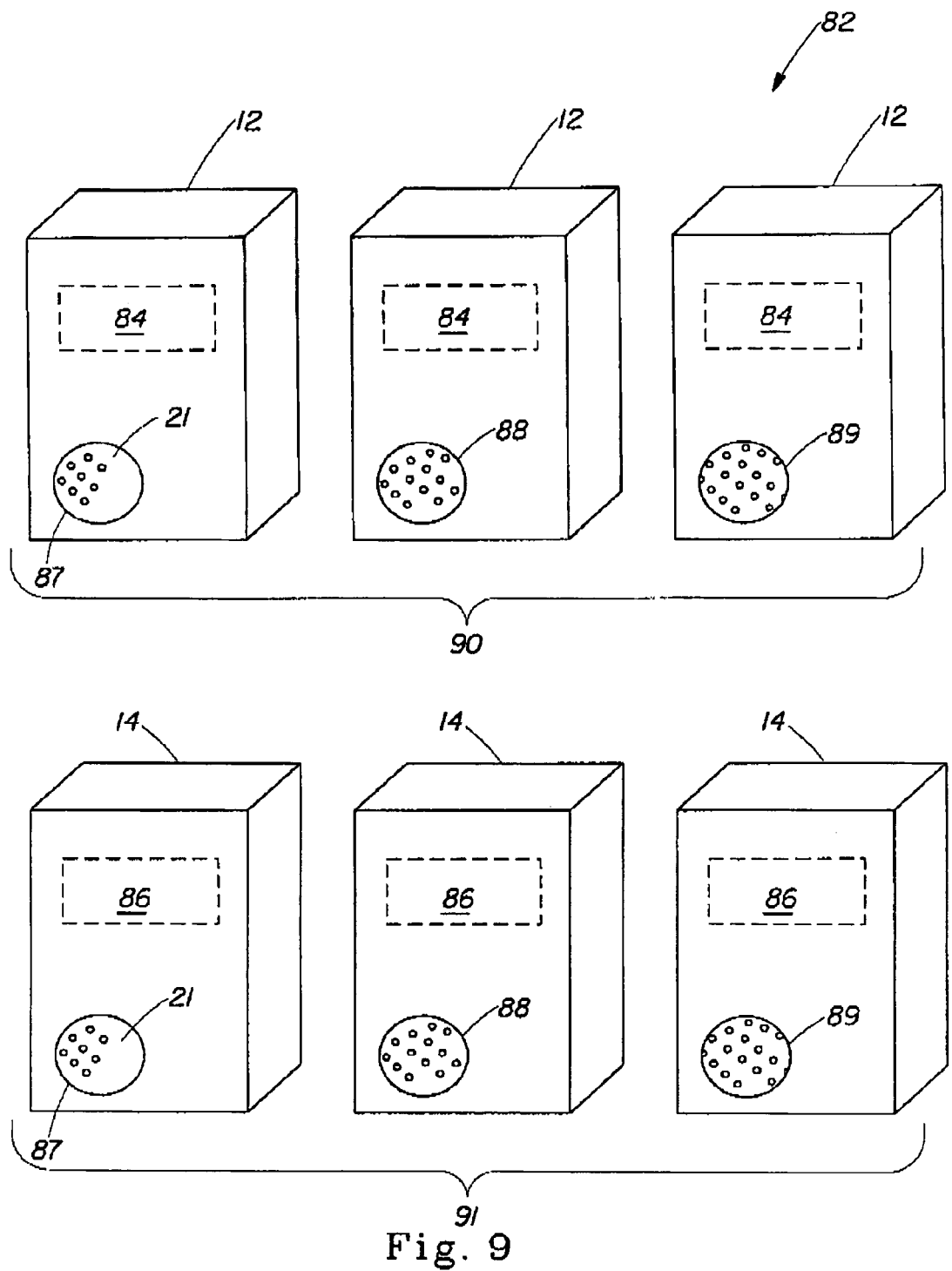
FIG. 9 is a view of an array of feminine hygiene articles of the present invention.

As shown in FIG. 9, a common indicator between two products 84, 86 can be placed on the package 12, 14 in a product array 90, 91. A display 82 of three product arrays signaling low absorbency 87, regular absorbency 88, and super absorbency 89 is shown. The array 90 includes a first product 84. The array 91 includes a second product 86. The first 84 and second 86 products are sold under distinct and different brand identifiers. Brand identifiers can be brand names, trademarked product identifiers, store brands, private label brands, trademarks, trade names, and the like. For example, as shown in FIG. 9, first product 84 can be a sanitary napkin sold under the ALWAYS® brand name and packaged in a first package 12. The second product 86 can be a tampon sold under the TAMPAX® brand name and packaged in a second package 14. Both product arrays 90,91 exhibit common indicators 21 on the package which signal low absorbency 87. In other words, as shown in FIG. 9, a first common indicator 21 which signals low absorbency 87 of the ALWAYS® mark is the same common indicator 21 for the second package 14 of the TAMPAX® brand name. Thus, both indicators 21 indicate low absorbency but are have different products and different brand names for each product. Likewise, both product arrays 90,91 exhibit common indicators 21 on the package which signal regular absorbency 88. Likewise, both product arrays 90,91 exhibit common indicators 21 on the package which super absorbency 89.

First 84 and second products 86 are separately packaged. By separately packaged is meant that the first 84 and second products 86 are not "bundled" or otherwise joined, attached, wrapped, or provided together for purchase by the consumer. The consumer can remove and/or purchase one or the other of the first 84 or second package 86 from the retail shelf display, without being required to remove or purchase the other package.

For example, in another non-limiting example, each brand identifier can have associated with it a common indicator 21, such as the surface area of the product being covered with a percentage of the indicator 21 as shown in detail in FIG. 9. The common indicator 21 can be a word, logo, emblem, graphic design, shape, color, or other mark.

For example, a display could have a product array of tampons, tampon applicators, and sanitary napkins. The product arrays consists of three absorbency line-ups having varying surface areas to denote the respective absorbencies of the products within the product arrays. The indicator is either the word "Tampax" or "Always". The first product array signals light absorbency, the second product array signals regular absorbency, and the third product array signals super absorbency. The first product array could have 30% of the surface area of the tampon covered with "Tampax" printed on the tampons and tampon applicators and 30% of the surface area of the sanitary napkin covered with "Always" printed on the sanitary napkins. The second product array could have 60% of the surface area of the tampon covered with "Tampax" printed on the tampons and tampon applicators and 60% of the surface area of the sanitary napkin covered with "Always" printed on the sanitary napkins. The third product array could have 90% of the surface area of the tampon covered with "Tampax" printed on the tampons and tampon applicators and 90% of the surface area of the sanitary napkin covered with "Always" printed on the sanitary napkins.

By using a common indicator 21, a manufacturer and marketer of a consumer product can communicate a performance characteristic, such as absorbency, without reference to printed text, pictures, diagrams, labels, and combinations thereof located on the package/wrapper. For example, for the embodiment shown in FIG. 9, a user of ALWAYS® sanitary napkins might also use TAMPAX® tampons of the same absorbency, and vice-versa. The manufacturer and marketer of one of either the first or second packaged product may wish to "link" their product to the other by communicating a common attribute in order to provide the consumer with an easy and intuitive signal for selecting the right product by the consumer. The indicator 21 can be used to communicate a level of scent, for example. Alternatively, in another embodiment, the indicator 21 may be used to communicate a common absorbent capacity, or a common odor control efficacy, or a common botanical extract, or a common skin health ingredient, or a common cleaning efficacy, for example. The common indicator 21 should be visible to the consumer at the point of sale.

By shelving first and second packaged products having different brand identifiers in close proximity on a store shelf, for example, in the same shelf tray or on the same end-of aisle display, the consumer is able to see the common indicator 21, and thereby be informed of a common attribute.

While the present invention is particularly useful in the product category of disposable absorbent articles, it can find equal utility in other categories such as oral care products, baby care products, fabric care products, pet care products, health care products, floor care products, car care products, laundry care products, electronic products. Non-limiting examples can include as first and second products, respectively, toothpaste and mouthwash, diapers and wipes, detergent and fabric softener, toilet tissue and facial tissue, snack foods and beverages, shampoo and conditioner, razor blades and shaving cream, dry mops and floor cleaning compositions, printers and ink cartridges, coffee and coffee filters, electronic gear and batteries, dog food and dog treats, and the like. For each of the above, a product from different brand names can be identified and paired together with a common indicator 21 for marketing at the point of sale. To take one example, CREST® toothpaste and SCOPE® mouthwash could be separately packaged and shelved, with each package carrying a common indicator 21 such as a picture or graphic design of a white tooth, or a word, such as "sparkle," or any other indicator 21 communicating a common attribute such as teeth cleaning or refreshing taste.

Referring to FIGS. 6-8, in any given product array, the indicators 21 may encompass the entire product or may encompass part of the product. For example, the indicators 21 may encompass one-fourth of the surface area of the tampon 20. In yet another example, the indicators 21 may encompass two-thirds of the surface area of the tampon 20.

The indicators 21 may be placed anywhere on the product. In other words, the overall trade dress of the product may use the indicators 21 in a variety of ways. Specifically, the indicators 21 may be placed anywhere on the product, e.g., on the top, sides, or bottom, or all three.

Indicators 21 can be any size or shape. Indicators 21 can be any size as long as the indicator 21 is able to be readily perceived by a consumer without having to refer to an external basis or calibration means for comparison. The indicator 21 can be circular, square, rectangular, triangular, arced, curved, or any other conceivable shape possible as long as the indicator 21 is able to be readily perceived by a consumer without having to refer to an external basis or calibration means for comparison. While the indicators 21 can be a wide range of shapes, it is preferred to use a member selected from the group consisting of straight grooves, spiral grooves, flower petals, ellipses, and mixtures thereof. Moreover, the indicator 21 can be a word, logo, emblem, graphic design, shape, color, mark, and mixtures thereof.

The indicator(s) 21 may be formed to have essentially identical size and shape as compared to other indicators 21 on the individual tampon 20. In one non-limiting example, the tampon has twenty indicators shaped like protuberances. Each protuberance is identical to the other protuberances. Alternatively, the indicator 21 may be formed to have various sizes and shapes as compared to another indicator 21 on the tampon 20. In one non-limiting example, the tampon may have twenty indicators. However, each indicator may have a different geometric shape. Additionally, each indicator may have a different size.

The number of indicators 21 and the distance over which the indicators 21 extend may vary. The number of indicators 21 may range from about 1 to about 50. Either an even or an odd number of indicators 21 can be present. For ease of manufacturing, it is preferred that the indicators 21 be equally spaced relative to one another. The indicators 21, however, may be unequally spaced relative to one another.

The distance between each indicator 21 depends upon the area of the product and the size and number of indicators 21.

Indicators 21 may be arranged randomly or in a pattern. For example, indicators 21 can be arranged to form any three-dimensional geometric pattern known including but not limited to diagonal lines, straight lines, checkerboard, flowers, ovals, circles, rectangles, trapezoids, triangles, cones, alphabet letters, and mixtures thereof. Alternatively, indicators 21 may be randomly arranged so that the multiplicity of indicators 21 may comprise merely a surface roughness in no apparent pattern. In addition, indicators 21 may be arranged such that the areas between the indicators 21 may form any geometric pattern known including but not limited to flowers, ovals, circles, rectangles, trapezoids, triangles, cones, alphabet letters, and mixtures thereof.

The indicator 21 may be formed to have essentially identical size and shape as compared to other indicators 21 in the same line-up. Moreover, while the use of increasing surface area, especially those having differing intensities, can be used to signal absorbency or other product performance characteristic such as size and strength, it is preferred to use differing surface areas which have indicators 21 of the same basic shape. For example, over the range of absorbencies: one groove which covers 10% of the surface area of the product can signal light absorbency; two grooves which covers 30% of the surface area of the product can signal regular absorbency; and three grooves which covers 60% of the surface area of the product can signal extra absorbency.

Alternatively, the indicator 21 may be formed to have various sizes and shapes as compared to another indicator 21 in the same line-up. In other embodiments, the indicators 21 may have shapes which are not similar as long as the indicators 21 on each product have an increased surface area which correlates with the increased absorbency. An important advantage of using a range of surface areas within the line-up is that continuity for the visual selection of the overall product line is maintained, while the user is provided with the desired intuitive selection, and usage means which is the object of this invention.

Referring to FIGS. 6-8, indicators 21 may be visually perceptible by techniques including, but not limited to, printing, stamping, coating, impregnating, embossing, folding, any known process that makes a visual, or even tactile, impression that indicates the indicator 21 having a surface area, or any combinations thereof. Various printing methods may be used to impart indicators 21 including, but not limited to, letterpress, flexography, gravure, offset lithography, screen, and inkjet. Indicators 21 can comprise printed indicia, such as ink-jet-printed figures, designs, lines or line segments, or embossed ridges or bumps, folds, pleats, or any other means known in the art for providing visible indications that impart an indictor 21 which covers the surface area of the tampon 20 and aids the user in choosing the proper absorbency tampon from a line-up of tampons.

In each case of the embodiments of the present invention shown in the FIGS. 6-8, one benefit to the user is the identification of the common functional characteristic across a product array in a line-up which aides the consumer in choosing the right product or products for her particular needs.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of articles, said array comprising:
   a.) a first article comprising
      i. an outer surface wherein said outer surface comprises an outer surface area and
      ii. a first identifier comprising a first surface area, wherein said first identifier is disposed on said first article and corresponds to a first performance characteristic;
   b.) a second article comprising
      i. an outer surface wherein said outer surface comprises an outer surface area and
      ii. a second identifier comprising a second surface area, wherein said second identifier is disposed on said second article and corresponds to a second performance characteristic;
   c.) wherein said first article is a different article than said second article; and
   d.) wherein said first surface area of said first article is the same as said second surface area of said second article.

2. The array of claim 1 wherein said first article is an absorbent article and said second article is a non-absorbent article.

3. The array of claim 1 wherein said first article is a first absorbent article and said second article is a second absorbent article.

4. The array of claim 3 wherein said first absorbent article is selected from the group consisting of tampons, tampon applicators, digital tampons, and mixtures thereof.

5. The array of claim 3 wherein said second absorbent article is selected from the group consisting of sanitary napkins, sanitary panties, interlabial devices, adult incontinence products, infant diapers, pantiliners, and mixtures thereof.

6. The array of claim 3 wherein said first absorbent article is selected from the group consisting of tampons, tampon applicators, digital tampons, and mixtures thereof and said second absorbent article is selected from the group consisting of sanitary napkins, sanitary panties, interlabial devices, adult incontinence products, infant diapers, pantiliners, and mixtures thereof.

7. The array of claim 3 wherein said first absorbent article and said second absorbent article is selected from the group consisting of tampons, tampon applicators, digital tampons, and mixtures thereof.

8. The array of claim 3 wherein said first absorbent article and said second absorbent article is selected from the group consisting of sanitary napkins, sanitary panties, interlabial devices, adult incontinence products, infant diapers, pantiliners, and mixtures thereof.

9. The array of claim 3 wherein said first absorbent article is a tampon and said second absorbent article is a sanitary napkin.

10. The array of claim 3 wherein said first absorbent article has a first absorbency and said second absorbent article has a second absorbency, wherein said second absorbency is greater than said first absorbency.

11. The array of claim 1 wherein said first article has a first brand and said second article has a second brand, wherein said first brand is different than said second brand.

12. The array of claim 1 wherein said outer surface area of said second article is the same as said outer surface area of said first article.

13. The array of claim 1 wherein said first identifier is a shape and said second identifier is a shape.

14. The array of claim 13 wherein said shape of said first identifier is the same shape as said shape of said second identifier.

15. The array of claim 13 wherein said shape of said first identifier is a different shape than said shape of said second identifier.

16. The array of claim 13 wherein said shape of said first identifier and said shape of said second identifier comprise surface aberrations.

17. The array of claim 16 wherein said surface aberrations are selected from the group consisting of protuberances, depressions, and mixtures thereof.

* * * * *

UNITED STATES PATENT AND TRADEMARK OFFICE
CERTIFICATE OF CORRECTION

PATENT NO. : 7,654,991 B2
APPLICATION NO. : 11/196840
DATED : February 2, 2010
INVENTOR(S) : Stellbrink et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Twenty-third Day of November, 2010

David J. Kappos
*Director of the United States Patent and Trademark Office*